(12) United States Patent
Wortz

(10) Patent No.: US 9,439,754 B2
(45) Date of Patent: Sep. 13, 2016

(54) PROSTHETIC CAPSULAR BAG AND METHOD OF INSERTING THE SAME

(71) Applicant: Omega Ophthalmics LLC, Lexington, KY (US)

(72) Inventor: Gary N. Wortz, Lexington, KY (US)

(73) Assignee: Omega Opthalmics LLC, Lexington, KY (US)

( * ) Notice: Subject to any disclaimer, the term of this patent is extended or adjusted under 35 U.S.C. 154(b) by 0 days.

(21) Appl. No.: 14/608,654

(22) Filed: Jan. 29, 2015

(65) Prior Publication Data

US 2015/0142106 A1    May 21, 2015

Related U.S. Application Data

(63) Continuation of application No. 14/551,544, filed on Nov. 24, 2014, which is a continuation of application No. 13/402,398, filed on Feb. 22, 2012, now Pat. No. 8,900,300.

(51) Int. Cl.
*A61F 2/14* (2006.01)
*A61F 2/16* (2006.01)

(52) U.S. Cl.
CPC .............. *A61F 2/14* (2013.01); *A61F 2/1648* (2013.01); *A61F 2/1694* (2013.01); *A61F 2/16* (2013.01); *A61F 2/1662* (2013.01)

(58) Field of Classification Search
CPC ........ A61F 2/14; A61F 2/16; A61F 2/16015; A61F 2/1694; A61F 2/1662; A61F 2/1648; A61F 2002/16901; A61F 2002/16902
See application file for complete search history.

(56) References Cited

U.S. PATENT DOCUMENTS

| | | |
|---|---|---|
| 4,073,014 A | 2/1978 | Poler |
| 4,435,856 A | 3/1984 | L'Esperance |
| 4,629,461 A | 12/1986 | Clayman et al. |
| 4,685,921 A | 8/1987 | Peyman |
| 4,731,078 A | 3/1988 | Stoy et al. |
| 4,888,012 A | 12/1989 | Horn et al. |

(Continued)

FOREIGN PATENT DOCUMENTS

| | | |
|---|---|---|
| EP | 0 337 390 | 10/1989 |
| EP | 0 294 039 | 7/1993 |

(Continued)

OTHER PUBLICATIONS

Postive Phase I/II Interim Data of Bimatoprost Sustained-Release Implant for IOP Therapy in Glaucoma, Nov. 16, 2015, http://www.allergan.com/NEWS/News/Thomson-Reuters/Positive-Phase-I-II-Interim-Data-of-Bimatoprost-Su.

(Continued)

*Primary Examiner* — David Isabella
*Assistant Examiner* — Dinah Baria
(74) *Attorney, Agent, or Firm* — Knobbe Martens Olson & Bear, LLP

(57) ABSTRACT

The present invention relates to a prosthetic capsular bag and method for inserting the same. The prosthetic capsular bag helps to maintain the volume of the natural capsular bag, thereby stabilizing the effective lens position of an IOL so that refractive outcomes may be improved with cataract surgery. The prosthetic capsular bag further provides an integrated refractive surface, providing a means for experimentally determining an effective lens position prior to inserting an IOL.

19 Claims, 8 Drawing Sheets

(56) References Cited

U.S. PATENT DOCUMENTS

| | | | |
|---|---|---|---|
| 4,892,543 | A | 1/1990 | Turley |
| 4,932,966 | A | 6/1990 | Christie et al. |
| 5,171,266 | A | 12/1992 | Wiley et al. |
| 5,222,981 | A | 6/1993 | Werblin |
| 5,275,623 | A | 1/1994 | Sarfarazi |
| 5,522,891 | A | 6/1996 | Klaas |
| 5,562,731 | A | 10/1996 | Cumming |
| 5,628,795 | A | 5/1997 | Langerman |
| 5,628,798 | A | 5/1997 | Eggleston et al. |
| 5,674,282 | A | 10/1997 | Cumming |
| 5,702,402 | A | 12/1997 | Brady |
| 5,800,533 | A | 9/1998 | Eggleston et al. |
| 5,968,094 | A | 10/1999 | Werblin et al. |
| 6,015,435 | A | 1/2000 | Valunin et al. |
| 6,027,531 | A | 2/2000 | Tassignon |
| 6,113,633 | A | 9/2000 | Portney |
| 6,117,171 | A | 9/2000 | Skottun |
| 6,136,026 | A | 10/2000 | Israel |
| 6,217,612 | B1 | 4/2001 | Woods |
| 6,235,055 | B1 * | 5/2001 | Chu ............ A61F 2/16 623/6.48 |
| 6,299,641 | B1 | 10/2001 | Woods |
| 6,322,589 | B1 | 11/2001 | Cumming |
| 6,413,276 | B1 | 7/2002 | Werblin |
| 6,428,574 | B1 | 8/2002 | Valunin et al. |
| 6,443,985 | B1 | 9/2002 | Woods |
| 6,454,801 | B1 | 9/2002 | Portney |
| 6,464,725 | B2 | 10/2002 | Skotton |
| 6,488,708 | B2 | 12/2002 | Sarfarazi |
| 6,503,276 | B2 | 1/2003 | Lang et al. |
| 6,524,340 | B2 | 2/2003 | Israel |
| 6,533,813 | B1 | 3/2003 | Lin et al. |
| 6,537,281 | B1 | 3/2003 | Portney |
| 6,537,317 | B1 | 3/2003 | Steinert et al. |
| 6,576,012 | B2 | 6/2003 | Lang |
| 6,645,246 | B1 | 11/2003 | Weinschenk, III et al. |
| 6,695,881 | B2 | 2/2004 | Peng et al. |
| 6,749,634 | B2 | 6/2004 | Hanna |
| 6,761,737 | B2 | 7/2004 | Zadno-Azizi et al. |
| 6,764,511 | B2 | 7/2004 | Zadno-Azizi et al. |
| 6,786,934 | B2 | 9/2004 | Zadno-Azizi et al. |
| 6,797,004 | B1 | 9/2004 | Brady et al. |
| 6,818,158 | B2 | 11/2004 | Pham et al. |
| 6,827,738 | B2 | 12/2004 | Willis et al. |
| 6,846,326 | B2 | 1/2005 | Zadno-Azizi et al. |
| 6,858,040 | B2 | 2/2005 | Nguyen et al. |
| 6,881,225 | B2 | 4/2005 | Okada |
| 6,884,261 | B2 | 4/2005 | Zadno-Azizi et al. |
| 6,899,732 | B2 | 5/2005 | Zadno-Azizi et al. |
| 6,921,416 | B2 | 7/2005 | Khoury |
| 6,926,736 | B2 | 8/2005 | Peng et al. |
| 6,960,230 | B2 | 11/2005 | Haefliger |
| 6,972,033 | B2 | 12/2005 | McNicholas |
| 7,001,374 | B2 | 2/2006 | Peyman |
| 7,025,783 | B2 | 4/2006 | Brady et al. |
| 7,029,497 | B2 | 4/2006 | Zhang et al. |
| 7,041,134 | B2 | 5/2006 | Nguyen et al. |
| 7,087,080 | B2 | 8/2006 | Zadno-Azizi et al. |
| 7,118,596 | B2 | 10/2006 | Zadno-Azizi et al. |
| 7,122,053 | B2 | 10/2006 | Esch |
| 7,125,422 | B2 | 10/2006 | Woods et al. |
| 7,144,423 | B2 | 12/2006 | McDonald |
| 7,198,640 | B2 | 4/2007 | Nguyen |
| 7,223,288 | B2 | 5/2007 | Zhang et al. |
| 7,226,478 | B2 | 6/2007 | Ting et al. |
| 7,452,362 | B2 | 11/2008 | Zadno-Azizi et al. |
| 7,452,378 | B2 | 11/2008 | Zadno-Azizi et al. |
| 7,662,179 | B2 | 2/2010 | Sarfarazi |
| 7,744,603 | B2 | 6/2010 | Zadno-Azizi et al. |
| 7,744,646 | B2 | 6/2010 | Zadno-Azizi et al. |
| 7,771,471 | B2 | 8/2010 | Dell |
| 7,780,729 | B2 | 8/2010 | Nguyen et al. |
| 7,806,929 | B2 | 10/2010 | Brown |
| 7,811,320 | B2 | 10/2010 | Werblin |
| 7,988,291 | B2 | 8/2011 | Ianchulev |
| 8,025,823 | B2 | 9/2011 | Pham et al. |
| 8,034,107 | B2 | 10/2011 | Stenger |
| 8,048,155 | B2 | 11/2011 | Shadduck |
| 8,052,752 | B2 | 11/2011 | Woods et al. |
| 8,062,361 | B2 | 11/2011 | Nguyen et al. |
| 8,088,161 | B2 | 1/2012 | Aharoni et al. |
| 8,100,965 | B2 | 1/2012 | Cumming et al. |
| 8,162,927 | B2 | 4/2012 | Peyman |
| 8,187,325 | B2 | 5/2012 | Zadno-Azizi et al. |
| 8,246,679 | B2 | 8/2012 | Nguyen et al. |
| 8,273,123 | B2 | 9/2012 | Ben Nun |
| 8,398,709 | B2 | 3/2013 | Ben Nun |
| 8,506,074 | B2 | 8/2013 | Gerband |
| 8,545,556 | B2 | 10/2013 | Woods et al. |
| 8,556,967 | B2 | 10/2013 | Sarfarazi |
| 8,574,295 | B2 | 11/2013 | Roholt |
| 8,579,971 | B2 | 11/2013 | Webb |
| 8,585,758 | B2 | 11/2013 | Woods |
| 8,663,235 | B2 | 3/2014 | Tassignon |
| 8,728,158 | B2 | 5/2014 | Whitsett |
| 8,778,022 | B2 | 7/2014 | Blum et al. |
| 8,821,166 | B2 | 9/2014 | Akura et al. |
| 8,834,565 | B2 | 9/2014 | Ben Nun |
| 8,900,300 | B1 | 12/2014 | Wortz |
| 8,915,588 | B2 | 12/2014 | Blum et al. |
| 8,931,896 | B2 | 1/2015 | Blum et al. |
| 9,005,283 | B2 | 4/2015 | Nguyen et al. |
| 9,039,760 | B2 | 5/2015 | Brady et al. |
| 9,072,600 | B2 | 7/2015 | Tran |
| 9,095,424 | B2 | 8/2015 | Kahook et al. |
| 9,124,796 | B2 | 9/2015 | Blum et al. |
| 9,125,736 | B2 | 9/2015 | Kahook et al. |
| 9,149,356 | B2 | 10/2015 | Sarfarazi |
| 9,186,243 | B2 | 11/2015 | Van Noy |
| 9,198,752 | B2 | 12/2015 | Woods |
| 9,289,287 | B2 | 3/2016 | Kahook et al. |
| 9,339,375 | B2 | 5/2016 | Lee et al. |
| 9,358,103 | B1 | 6/2016 | Wortz et al. |
| 2001/0047204 | A1 | 11/2001 | Zhou et al. |
| 2001/0051825 | A1 | 12/2001 | Peterson |
| 2002/0128710 | A1 | 9/2002 | Eggleston |
| 2002/0143395 | A1 | 10/2002 | Skottun |
| 2002/0173846 | A1 | 11/2002 | Blake et al. |
| 2003/0004569 | A1 | 1/2003 | Haefliger |
| 2003/0050695 | A1 | 3/2003 | Lin et al. |
| 2003/0187505 | A1 | 10/2003 | Liao |
| 2004/0082993 | A1 | 4/2004 | Woods |
| 2004/0082995 | A1 | 4/2004 | Woods |
| 2004/0167622 | A1 | 8/2004 | Sunalp et al. |
| 2005/0021138 | A1 | 1/2005 | Woods |
| 2005/0085907 | A1 | 4/2005 | Hanna |
| 2005/0107875 | A1 | 5/2005 | Cumming |
| 2005/0113911 | A1 | 5/2005 | Peyman |
| 2005/0222577 | A1 * | 10/2005 | Vaquero ............ A61F 2/1678 606/107 |
| 2005/0234285 | A1 | 10/2005 | Khoury |
| 2006/0047339 | A1 | 3/2006 | Brown |
| 2006/0095128 | A1 | 5/2006 | Blum et al. |
| 2006/0212116 | A1 | 9/2006 | Woods |
| 2006/0259139 | A1 | 11/2006 | Zadno-Azizi et al. |
| 2007/0027538 | A1 | 2/2007 | Aharoni et al. |
| 2007/0027541 | A1 | 2/2007 | Aharoni et al. |
| 2007/0032868 | A1 | 2/2007 | Woods |
| 2007/0083261 | A1 | 4/2007 | Colvard |
| 2007/0093892 | A1 | 4/2007 | Mackool |
| 2007/0118216 | A1 | 5/2007 | Pynson |
| 2007/0123981 | A1 * | 5/2007 | Tassignon ............ A61F 2/1613 623/6.12 |
| 2007/0162118 | A1 | 7/2007 | Rozakis et al. |
| 2007/0213816 | A1 | 9/2007 | Sarfarazi |
| 2008/0221676 | A1 | 9/2008 | Coleman et al. |
| 2009/0005864 | A1 | 1/2009 | Eggleston |
| 2009/0182423 | A1 | 7/2009 | Zheng |
| 2010/0030225 | A1 * | 2/2010 | Ianchulev ............ A61B 3/0033 606/107 |
| 2010/0211171 | A1 | 8/2010 | Sarfarazi |
| 2010/0228344 | A1 * | 9/2010 | Shadduck ............ A61F 2/1648 623/6.18 |
| 2010/0280609 | A1 | 11/2010 | Simonov et al. |

(56) References Cited

U.S. PATENT DOCUMENTS

| | | |
|---|---|---|
| 2011/0015541 A1* | 1/2011 | Padrick ............ G02C 7/022 600/558 |
| 2011/0153014 A1 | 6/2011 | Zhang et al. |
| 2011/0181834 A1 | 7/2011 | Gerbaud |
| 2012/0179249 A1 | 7/2012 | Coleman |
| 2012/0226351 A1 | 9/2012 | Peyman |
| 2013/0116781 A1 | 5/2013 | Ben Nun |
| 2013/0190868 A1 | 7/2013 | Kahook et al. |
| 2013/0310931 A1 | 11/2013 | Kahook et al. |
| 2014/0052246 A1 | 2/2014 | Kahook et al. |
| 2014/0067059 A1 | 3/2014 | Webb |
| 2014/0172089 A1 | 6/2014 | Lee et al. |
| 2014/0228949 A1 | 8/2014 | Argento et al. |
| 2014/0371852 A1 | 12/2014 | Aharoni et al. |
| 2015/0127102 A1 | 5/2015 | Wortz |
| 2015/0289970 A1 | 10/2015 | Akura |
| 2015/0335420 A1 | 11/2015 | Blum et al. |
| 2015/0366656 A1 | 12/2015 | Wortz et al. |
| 2015/0366659 A1 | 12/2015 | Wortz et al. |
| 2016/0008126 A1 | 1/2016 | Salahieh et al. |
| 2016/0058553 A1 | 3/2016 | Salahieh et al. |
| 2016/0113760 A1 | 4/2016 | Conrad |

FOREIGN PATENT DOCUMENTS

| | | |
|---|---|---|
| EP | 0 528 325 | 12/1996 |
| EP | 0 732 090 | 6/2002 |
| EP | 1 499 264 | 8/2006 |
| EP | 1 100 411 | 11/2006 |
| EP | 1 653 886 | 1/2008 |
| EP | 1 852 090 | 1/2009 |
| EP | 1 475 055 | 4/2010 |
| EP | 1 438 930 | 9/2011 |
| EP | 2 315 559 | 1/2012 |
| EP | 2 412 337 | 2/2012 |
| EP | 1 296 616 | 5/2012 |
| EP | 1 906 881 | 8/2012 |
| EP | 1 694 253 | 8/2013 |
| EP | 2 851 038 | 3/2015 |
| EP | 2 512 374 | 11/2015 |
| JP | 02-011134 | 1/1990 |
| JP | 2005-143886 | 6/2005 |
| WO | WO 98/17205 | 4/1998 |
| WO | WO 02/071983 | 9/2002 |
| WO | WO 2006/124016 | 11/2006 |
| WO | WO 2010/002215 | 1/2010 |
| WO | WO 2015/044235 | 4/2015 |
| WO | WO 2015/195825 | 12/2015 |

OTHER PUBLICATIONS

Notice of Allowance issued in Japanese Patent Application No. 2014-558790, dated Jun. 25, 2015, in 3 pages.

Office Action issued in Japanese Patent Application No. 2014-558790, dated Feb. 3, 2015, in 9 pages.

Becker et al., "Accuracy of lens power calculation and centration of an aspheric intraocular lens", Ophthalmologel, Oct. 2006, vol. 103, Issue 10, pp. 873-876.

International Search Report and Written Opinion issued in PCT Application No. PCT/US2013/026820, dated May 31, 2013.

Kleinmann, "Open-Capsule Device for PCO Prevention", Oct. 17, 2013.

Kleiman et al., "Post-operative Results With Implantation of the Acrysof SA-60 Intraocular Lens into the Ciliary Sulcus", ARVO Annual Meeting Abstract Search and Program Planner, May 2002, vol. 2002, Abstract No. 380.

Koeppl, C. et al., "Change in IOL position and capsular bag size with an angulated intraocular lens early after cataract surgery", Journal of Cataract and Refractive Surgery, Feb. 2005, vol. 31, Issue 2, pp. 348-353.

Krader, "Small-aperture optic IOL broadens range of vision", Dec. 1, 2014.

Lim et al., "Surgical management of late dislocated lens capsular bag with intraocular lens and endocapsular tension ring", Journal of Cataract and Refractive Surgery, Mar. 2006, vol. 31, Issue 3, pp. 533-535.

"Tracking IOL With an IOL," Sep. 15, 2014.

Wirtitsch et al., "Effect of haptic design on change in axial lens position after cataract surgery", Journal of Cataract and Refractive Surgery, Jan. 2004, vol. 30, Issue 1, pp. 45-51.

International Preliminary Report on Patentability in PCT App. No. PCT/US2013/026820, dated Aug. 26, 2014.

International Search Report and Written Opinion issued in PCT Application No. PCT/US2015/036263, dated Oct. 7, 2015.

Office Action issued in European Application No. 13710641.5, dated Oct. 1, 2015, in 5 pages.

International Search Report and Written Opinion issued in PCT Application no. PCT/US2015/065887, dated Apr. 6, 2016.

* cited by examiner

PROSTHETIC CAPSULAR BAG AND METHOD OF INSERTING THE SAME

CROSS-REFERENCE TO RELATED APPLICATIONS

This application is a continuation of U.S. patent application Ser. No. 14/551,544, filed Nov. 24, 2014, which is hereby incorporated by reference in its entirety and which is a continuation of U.S. patent application Ser. No. 13/402,398, filed Feb. 22, 2012 and issued as U.S. Pat. No. 8,900,300 on Dec. 2, 2014.

BACKGROUND OF THE INVENTION (a) Field of the Invention

The present invention relates to a prosthetic capsular bag and method for inserting the same.

(b) Description of the Related Art

Cataract surgery is one of the most successfully and most frequently performed surgical procedures in the US. Each year, millions of people achieve a dramatic improvement in their visual function thanks to this procedure. With the increasing proportion of the US population reaching their retirement years, there is expected to be a doubling of the demand for cataract surgery over the next twenty years from 3.3 million to over 6 million annually. This increased demand will require more ophthalmologists to be trained to perform cataract surgery as well as each trained ophthalmologist to perform more cataract surgeries each year.

In addition to the increase in demand for cataract surgery, there have been many technological advances that have increased patient expectations and requirements for the surgery. The procedure takes a short amount of time to perform, and patients expect quick recovery of visual function. Patients are also asking their ophthalmologist to give them restoration of more youthful vision without glasses through the use of multifocal lenses, presbyopia correcting lenses, toric lenses, and monovision to name a few. The use of these lenses requires perfect technique, perfect preoperative measurements, and a dose of good fortune to ensure patient satisfaction. In fact, as many as 20-50% of patients will typically require glasses or follow up refractive surgical enhancements to achieve their desired refractive endpoint. The reason for this high amount of refractive unpredictability comes from the final resting position of the lens implant within the eye. This is mathematically expressed as the effective lens position ("ELP"), and can be quite variable and unpredictable in the current state of cataract surgery. Recently, hundreds of millions of dollars have been invested into developing highly sophisticated femtosecond laser systems that will be able to more precisely create the cataract incisions with the stated goal of lessening the variability of the ELP and thus aiding in better refractive outcomes. However, as good as the laser is, it does not account for the major problem plaguing the variability of the ELP, which is the volumetric difference between the cataract, natural capsular bag and intraocular lens implant, or IOL.

SUMMARY OF THE INVENTION

The present invention relates to a prosthetic capsular bag and method for inserting the same. The prosthetic capsular bag addresses the above mentioned problem by helping to maintain the volume of the natural capsular bag, thereby stabilizing the effective lens position of the IOL and improving refractive outcomes with cataract surgery. The prosthetic capsular bag further provides an integrated refractive surface, providing a means for experimentally determining an effective lens position prior to inserting an IOL. Herein, the prosthetic capsular bag of the present invention is referred to as a Perfect Prosthetic Lenticular Capsule or "PPL-C."

In one embodiment, the present invention is a prosthetic capsular bag for insertion into an eye, the prosthetic capsular bag comprising an anterior surface including an opening, and a posterior surface, wherein at least a portion of the posterior surface is a refractive surface. In this embodiment, the prosthetic capsular bag is adapted to contain an intraocular lens.

In a further embodiment, the present invention is a prosthetic capsular bag for insertion into an eye, the prosthetic capsular bag having a generally discoid shape including a posterior surface, an anterior surface including an opening, and a flange extending radially from the opening.

In another embodiment, the present invention is a prosthetic barrier for separating an anterior segment and poster segment in an eye, the barrier having a generally discoid shape including a posterior surface, an anterior surface including an opening, and an exterior contour flange extending radially from the opening.

In a further embodiment, the present invention is a method for inserting and positioning an intraocular lens into a patient's eye comprising: (a) inserting a prosthetic capsular bag into the patient's eye, the prosthetic capsular bag including an anterior surface, the anterior surface having an opening, and a posterior surface, wherein at least a portion of the posterior surface is a refractive surface; (b) determining the position of the refractive surface; (c) selecting an intraocular lens based on the determined position of the refractive surface; and (d) inserting the intraocular lens into the prosthetic capsular bag.

BRIEF DESCRIPTION OF THE DRAWINGS

A better understanding of the present invention will be had upon reference to the following description in conjunction with the accompanying drawings, wherein.

DETAILED DESCRIPTION OF THE PREFERRED EMBODIMENT

Figure 1:
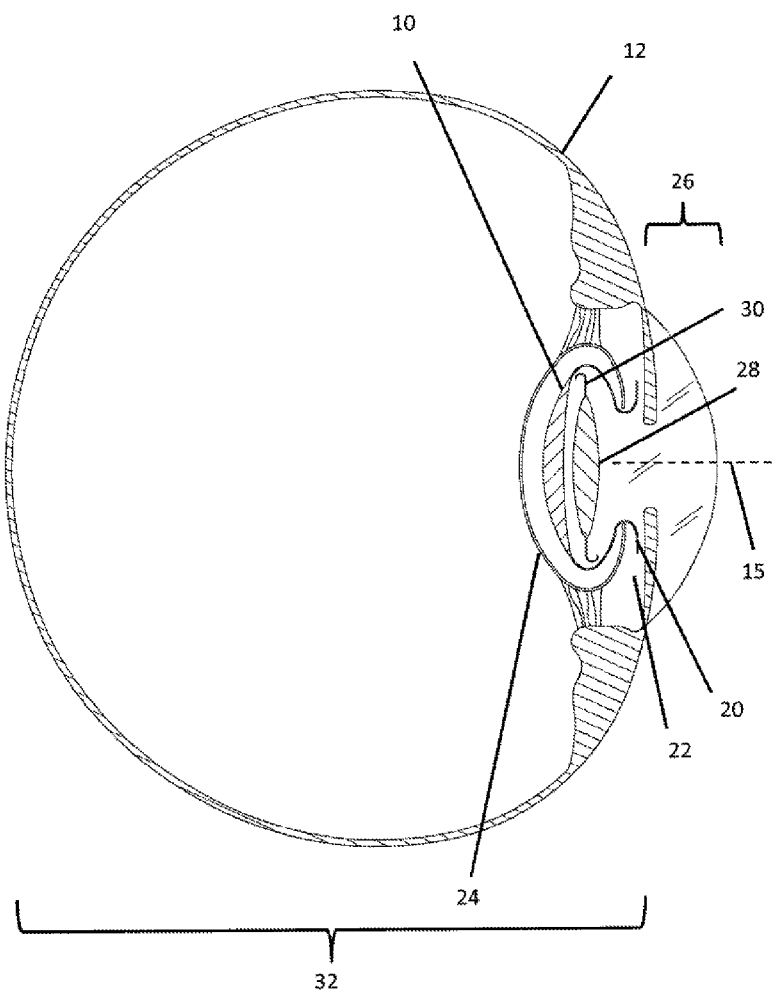
FIG. 1 depicts a cross-sectional side view of an eye including a first embodiment of a PPL-C containing an IOL.
Figure 2:
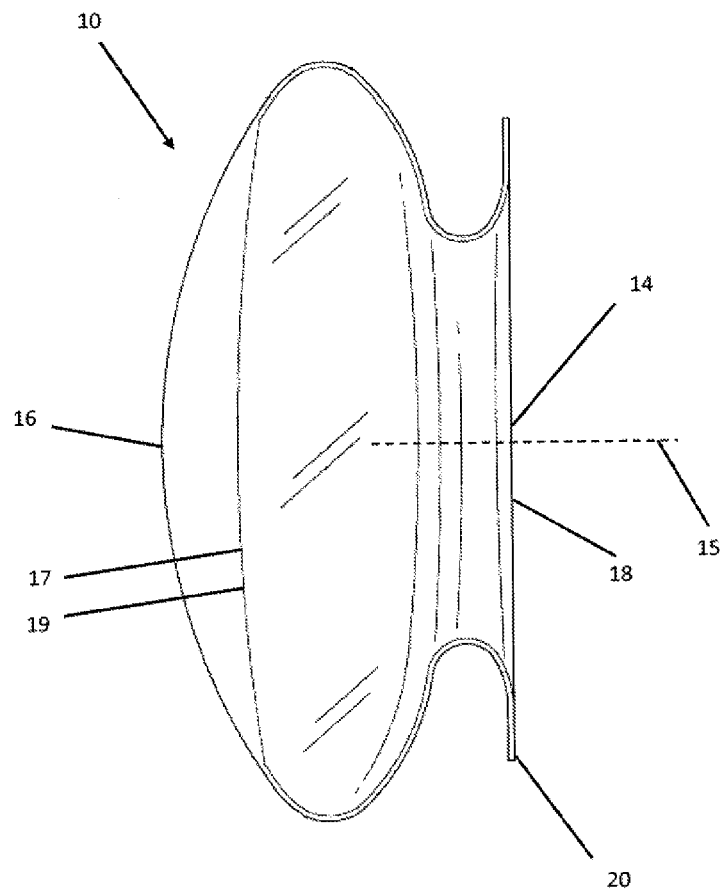
FIG. 2 depicts a side elevation view of the first embodiment of the PPL-C.
Figure 3:
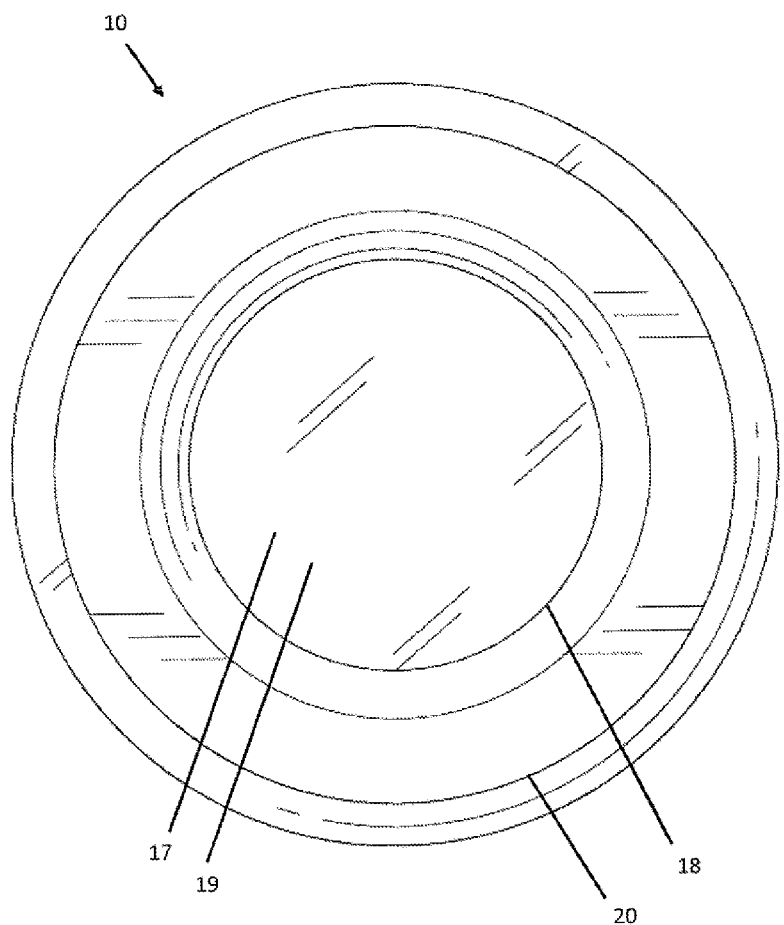
FIG. 3 depicts an anterior plan view of the first embodiment of the PPL-C.

With reference to FIGS. 1-3, the PPL-C 10 of the instant invention is shown approximating the size and shape and volume of a natural human lens. Its dimensions would be variable, so that physicians may order an implant that most closely matches the lens of the eye 12 being operated on.

The human lens varies in thickness from approximately 3.5 mm to 5.5 mm. A natural lens tends to be thicker in more hyperopic eyes and thinner in more myopic eyes. Also, the lens thickens over time and increased age is associated with a thicker lens on average. The diameter of the human lens is approximately 9 mm. Therefore, in one embodiment, the PPL-C 10 would be a substantially discoid shape of approximately 4.5 mm in thickness by 9 mm in diameter. For purposes of clarity, the thickness of the PPL-C 10 is the distance between the anterior surface 14 and posterior surface 16 of the PPL-C 10 along the visual axis 15. The anterior surface 14 contains a circular opening 18 approximately 6 mm in diameter, with an exterior contour, such as, for example, a 1 mm flange 20, surrounding and extending radially from the opening 18. The flange 20 would further assist in stabilization and centration of the PPL-C 10 by extending into and fitting within the ciliary sulcus 22. This size of PPL-C 10 would function to fit precisely within the capsulorhexis created by a femtosecond laser.

At least a portion of the inner face 17 of the posterior surface 16 of the PPL-C 10 would be made of a refractive surface so that a pseudophakic refraction could be performed intraoperatively with a known lens already inside the eye, e.g. the posterior refractive surface 19. In a preferred embodiment, as shown in FIGS. 1-3, substantially the entire inner face 17 would be made of a low power refractive surface (for example +1D). While the posterior refractive surface 19 is generally discussed in terms of a +1D surface, it may be made of any and all lens powers and designs that are currently known in the art of intraocular lenses. This includes, but is not limited to: spherical, aspheric, wavefront, convex, concave, multifocal (diffractive, refractive, zonal), toric, accommodative, UV filtering, and diffractive chromatic aberration reducing lenses, and optical powers ranging from +30 to −30 diopters.

The PPL-C 10 is adapted to be implanted within the eye and is preferably made of a biologically-compatible material that would be inert inside the eye. It is preferably deformable so as to be folded and inserted via an injection system through a corneal incision ranging between about 0.1 mm and 10 mm, preferably between about 1.5 mm and 3 mm. The size of the corneal incision varies based on several factors, including the volume of the PPL-C 10, its plasticity, and the volume of the injection cartridge through which the PPL-C 10 will be delivered. The capsulorhexis must be about equal to or less than the dilated diameter of the patient's iris as the opacity of the iris forms a natural barrier for the capsulorhexis created by a femtosecond laser. A capsulorhexis created manually is typically of the same size, as direct visualization of the rhexis boundary is advisable throughout the creation process. The capsulorhexis ranges between about 3 mm and 8 mm, preferably between about 4 mm and 7 mm. During implantation, the folded PPL-C 10 passes through the corneal incision, through the capsulorhexis, and into the patient's natural capsular bag 24. The PPL-C 10 preferably also possesses sufficient elasticity to resume its pre-folded shape once positioned inside the eye. Current intraocular lenses are made of various materials including silicone, collamer, and acrylic that have these capabilities. In preferred embodiments, the material used for the PPL-C 10 is a biologically-compatible, optically clear material similar or identical to those used in foldable intraocular lenses.

Figure 8:
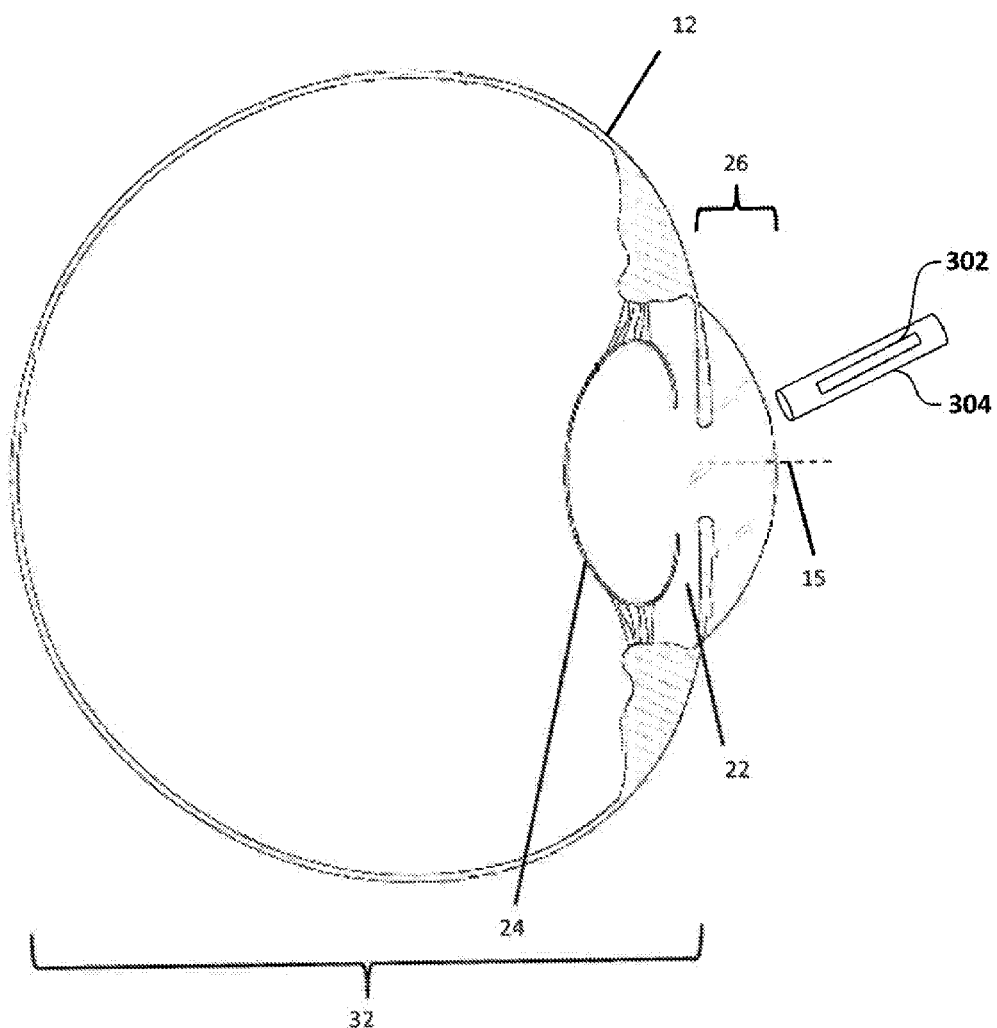
FIG. 8 illustrates a cross-sectional side view of an eye with an embodiment of an injection system comprising a PPL-C in a folded state.

With reference to FIG. 8, PPL-C 10 would preferably be inserted into the patient's eye 12 through the use of an injection system 304. The injection system 304 would allow the PPL-C 10 to be automatically folded into a smaller shape 302 as it was advanced so as to allow it to fit through an incision much smaller than the diameter of the unfolded PPL-C 10. The inventor believes that injection systems 304 already developed through which IOLs are injected into the eye, which comprise a cylindrical cartridge and an advancement rod on a screw type advancement system or plunger advancement system, would be suitable for use with the PPL-C 10.

The PPL-C 10 is preferably inserted into a patient's eye 12 with the use of a laser. A femtosecond laser would be used to create the capsulorhexis, likely after the same device was used to make the other incisions including the main wound, the paracentesis and any corneal or limbal relaxing incisions as necessary. The cataract, i.e., the patient's natural lens, would then be removed using techniques known in the art. The residual cortex would be removed using technique known in the art, such as via inspiration/aspiration. An aphakic refraction would be completed using an intraocular refracting device such as, for example, the Wavetec ORA system. An IOL calculation would be performed using an algorithm such as, for example, the Mackool algorithm. Then, the patient's natural capsular bag 24 and anterior segment 26 would be filled with viscoelastic material, and the PPL-C 10 would be loaded into the injection device. It would be folded into a small tubular shape and injected into the natural capsular bag 24. The viscoelastic material would be removed from behind the PPL-C, and from the anterior segment 26. A psuedophakic refraction would be done with a system similar to a standard auto-refractor, or the intraoperative Wavetec ORA system. This calculation would need to be done using approved protocols.

An example refraction using an approved protocol, and accompanying background information, is discussed herein. Current state of the art requires multiple independent variables to be measured so that the dependent variable of effective lens position can be estimated. These independent variables in the Holladay 2 formula (one of the most popular modern formulas) are in decreasing order of importance include: axial length, average keratometric power, horizontal white to white, refraction, anterior segment depth, lens thickness, and age. These variables are then used to estimate the ELP. However, this is simply an estimation or prediction. If this prediction is incorrect, the post-operative refractive outcome will be compromised. Therefore, emphasis should be placed on the ability to determine the ELP rather than estimating it. The PPL-C 10 will help determine the ELP in two different ways, as described in the procedure below.

Figure 4:
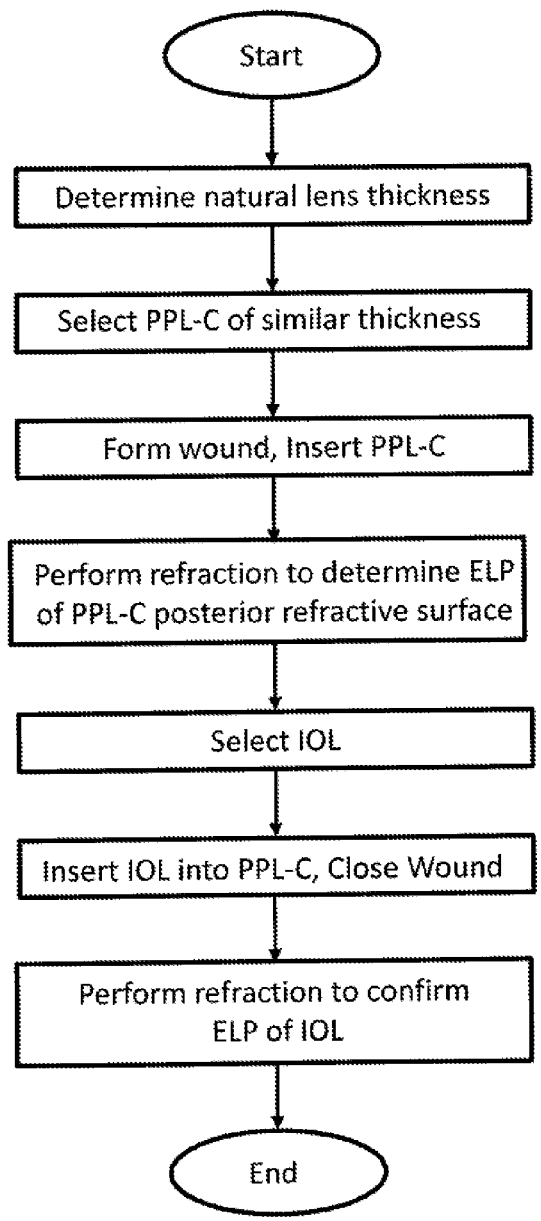
FIG. 4 is a flowchart of a method for inserting and positioning an intraocular lens into a patient's eye.

FIG. 4 is a flowchart depicting a method for inserting and positioning an intraocular lens into a patient's eye. First, the lens thickness of a patient's natural lens is determined pre-operatively using known techniques. Next, a PPL-C 10 of similar thickness will be chosen for implantation. The goal will be to select a PPL-C 10 sized such that the inner face 17 of the PPL-C 10 at the same location as the posterior surface of the patient's natural lens. When an IOL 28 is inserted within the PPL-C adjacent to the inner face 17 and centered within the PPL-C 10, that IOL 28 will be positioned in substantially the identical location previously occupied by the patient's natural lens.

A femtosecond laser is used to create the main wound, the paracentesis and any corneal or limbal relaxing incisions as necessary, and the capsulorhexis. The patient's natural lens is then removed using techniques known in the art. The residual cortex is removed using techniques known in the art, such as via inspiration/aspiration. Then, the patient's natural capsular bag 24 and anterior segment 26 are filled with viscoelastic material, and the PPL-C 10 inserted into the natural capsular bag 24. The viscoelastic material is then removed from behind the PPL-C, and from the anterior segment 26 in preparation for performing a psuedophakic refraction.

By being able to identify and control the position of the IOL 28, choosing an IOL 28 is no longer dependent upon the 7 variables for ELP. Rather, via theoretical vergence formulas, the exact IOL 28 needed to provide a desired refractive outcome can be specifically calculated with keratometric power, effective lens position and axial length. The current weakness of the formulas in place is due to the inability to accurately predict ELP. To confirm the pre-operative theoretical calculation is correct, a refraction is performed in the operating room once the PPL-C 10 is implanted in the patient's eye via a Wavetec ORA system, retinoscopy or by other known methods. The refraction will technically be a pseudophakic refraction as the posterior refractive surface 19 of the PPL-C 10 will have a refractive power, such as, for example, +1 diopter.

A method of determining the correct intraocular power for a piggyback lens is calculated by first determining the power of the IOL 28 to be implanted using the following equation:

$$IOLe = \frac{1336}{\frac{1336}{\frac{1000}{\frac{1000}{PreRx} - V} + Ko} - ELPo} - \frac{1336}{\frac{1336}{\frac{1000}{\frac{1000}{DPostRx} - V} + Ko} - ELPo}$$

ELP o=effective lens position.
K o=net corneal power.
IOL e=IOL power.
V=vertex distance.
PreRx=pre-op refraction. (Also can represent the intra-operative refraction after PPL-C has been placed)
DPostRx=desired post-op refraction.

The Effective Lens Position (ELPo) is the distance from the secondary principal plane of the cornea to the principal plane of the thin-IOL equivalent. The keratometric power of the cornea (Kk) is converted to the net optical power of the cornea (Ko) as follows: Ko=Kk*0.98765431. For example, if the Kk is 44.50 D, Ko=44.50 D*0.98765431=43.95 D. The net optical power of the cornea (Ko) would then be 43.95 D.

By comparing pre-operative theoretical IOL calculations with the aphakic refraction, the PPL-C refraction, and the post-IOL implantation refraction, surgeons can greatly improve the accuracy of their post-operative refractive outcomes.

Once the appropriate IOL 28 is selected, the PPL-C 10 and anterior segment 26 are refilled with viscoelastic material and, based on the residual refractive error, the appropriate IOL 28 is selected and inserted into the PPL-C 10. The viscoelastic material is then removed from the eye, and the wounds closed through standard methods of hydration or suturing. A final confirmatory refraction would be completed, taking great effort to ensure normal intraocular pressure, as this can affect the position of the PPL-C 10 and IOL 28 inside the eye. If there were found to be a significant error at this point, the surgeon would still have the luxury of removing the implanted IOL and replacing it with one of a more desirable refractive power, without risking damage to the fragile natural capsular bag 24, due to the protective nature of having the IOL 28 contained within the PPL-C 10.

The PPL-C 10 provides an enhanced ability to achieve desired refractive targets, with a side benefit of increased safety. This implant will provide these advantages in several ways.

First, the PPL-C 10 provides centration of the IOL 28 along the visual axis 15. A femtosecond cataract laser system has the ability to center the capsulorhexis around the visual axis 15 of the patient rather than the optical center of the cataract. The capsulorhexis is ultimately what will center the PPL-C 10 as this is the opening through which the PPL-C 10 will be inserted. The capsulorhexis is essentially juxtaposed at the center of the PPL-C 10, centering the PPL-C 10 and being stabilized via the flange 20 extending into and fitting within the ciliary sulcus 22. The flange 20 mechanically retains the PPL-C 10 centered on the patient's visual axis 15 and prevents future movement or migration of the PPL-C 10.

Centration of the IOL 28 on the visual axis 15 is extremely important to the visual function of the IOL 28 and the benefit the patient receives. Aspheric lenses have made decentration more tolerable, however centration is absolutely vital to the best visual performance of multifocal intraocular lenses. Decentration of less than 1 mm can cause significant morbidity, so much so that surgical intervention including laser pupiloplasty, IOL repositioning and IOL exchange are often needed. The PPL-C 10 is centered along the visual axis 15 via the capsulorhexis. An IOL 28 commonly includes haptics 30 which can engage opposed interior surfaces within the PPL-C 10 to maintain the centered position of the IOL 28. The outer diameter of the IOL 28, when unfolded and including the haptics 30, is substantially equal to the inner diameter of the PPL-C 10. Therefore, the IOL 28 will be in physical contact with the peripheral internal surface of the PPL-C 10, which maintains the centered position of the IOL 28 within the PPL-C 10 and also within the visual axis 15.

Second, the PPL-C 10 provides a prosthetic barrier between the anterior segment 26 and posterior segment 32 of the eye in the case of inadvertent rupture of the posterior surface of the natural capsular bag 24, or after planned YAG laser posterior capsulotomy. Despite the overall success of cataract surgery, there is still about a 2% surgical complication rate utilizing modern techniques, although this varies among individual surgeons. Residents in ophthalmology training programs have historically had complication rates around 4-7%. Most complications from cataract surgery are caused by inadvertent rupture of the natural capsular bag 24 which houses the cataract. The natural capsular bag 24 also provides an important anatomical barrier within the eye. It divides the anterior segment 26 from the posterior segment 32. The posterior segment 32 contains the vitreous body, retina, optic nerve and the central retinal artery and vein. A violation of the integrity of the barrier provided by the natural capsular bag 24 allows fluid communication between the anterior and posterior segments 26, 32, and potentially the ocular surface. Vitreous may then flow out of the posterior segment 32 according to pressure gradients, flowing from high pressure toward low pressure. This typically causes vitreous to flow directly to the surgical incision site. Vitreous can prevent wound healing if it shifts to the surgical incision site, and more significantly can provide a conduit for microbial infections to proceed directly to the posterior segment 32. In addition to the problems caused by vitreous, a break or tear in the natural capsular bag 24 can prevent the stable implantation of an IOL within the posterior segment 32. Alternatively, surgeons can place an IOL 28 in the ciliary sulcus 22 or the anterior chamber, although each of these has their own potential complications associated with them. Therefore it is of utmost importance to keep the natural capsular bag 24 intact as there are currently no methods to consistently reestablish the integrity of the natural capsular bag 24 once it has been compromised. Should the natural capsular bag 24 be compromised, the PPL-C 10 may serve as a prosthetic barrier between the anterior segment 26 and posterior segment 32.

About 30% of all implanted intraocular lenses will develop visually significant posterior capsular opacification. If this develops, a YAG laser is used to create an opening in the posterior surface of the natural capsular bag 24 to remove this opaque membrane. However, once the hole in the natural capsular bag 24 is created, the barrier between the vitreous and the anterior segment 26 has been lost. Thus, if the lens needs to be removed after a YAG laser posterior capsulotomy has been performed, it makes the chances for serious complications rise dramatically. However, if a PPL-C 10 is placed in the natural capsular bag 24 and a YAG laser posterior capsulotomy has been performed, there is still an adequate barrier for the vitreous in place. In addition, the haptics 30 which hold the IOL 28 in place inside the PPL-C 10 are not prone to scar formation, thus making future lens removal much easier and decreasing the risk for complications during IOL exchange.

Third, the PPL-C 10 limits the chronic capsular opacification that takes place in the natural capsular bag 24 and can cause refractive shifts due to ELP change, anterior capsular phimosis, and visually significant posterior capsular opacification. After cataract surgery has been performed, the natural capsular bag 24 undergoes chronic changes. These changes are largely due to the presence of lens epithelial cells that remain on the natural capsular bag 24 after surgery. These epithelial cells continue to grow and can cause problems. For example, the anterior surface of the natural capsular bag 24 can fibrose and contract over time causing a progressively smaller aperture overtop of the lens. If the entire natural capsular bag 24 becomes fibrotic, and phimosis persists, there can be zonular dehiscence and changes to the effective lens position over time. In addition, about 30% of the time, the posterior surface of the natural capsular bag 24 becomes significantly opacified requiring a YAG laser posterior capsulotomy. The effect of limiting epithelial cell migration and propagation would largely be mediated by the type of material used in forming the PPL-C 10, however hydrophobic acrylic materials tend to be most efficacious of all known and used IOL materials.

Fourth, the PPL-C 10 helps maintain the effective lens position of an IOL 28 implanted into the eye. Precisely matching the preoperative dimensions of the cataract with the PPL-C 10 enhances a physician's ability to predict the ELP of the lens implant. Currently, the ELP of an IOL 28 is estimated based on a number of factors, including the depth of the anterior segment 26, lens thickness, and white to white diameter, among others. However, these measurements are simply used to predict the ELP. The accuracy of the prediction is actually quite low, resulting in only 50% of patients being within a tolerable level of their refractive goal post-cataract surgery. While other dimensions of the eye required for IOL calculation can be measured quite precisely and accurately, the ELP has remained the elusive last great variable to conquer in the quest for highly accurate and predictable IOL calculations for cataract surgery.

The reason for the great variability in the ELP is due to the volumetric difference between the cataract and the IOL. The average thickness of the human cataract at age 65 is approximately 4.5 mm, however this varies from patient to patient. In contrast, an IOL 28 is typically less than 1 mm thick. This volumetric difference allows for pressure differentials between the posterior segment 32 and the anterior segment 26, as well as contraction of the natural capsular bag 24 to shift the final resting position of the IOL 28. The lens thickness will be measured preoperatively and a PPL-C 10 with a corresponding volume and thickness will be implanted. By implanting a PPL-C 10, the volume of the natural capsular bag 24 is effectively held constant. It resists forces that would otherwise shift it and its contents anteriorly or posteriorly. This stability of lens capsule volume will make IOL calculations much more accurate.

Fifth, the PPL-C 10 allows for an intraoperative pseudophakic refraction while still allowing another IOL to be implanted without explanting the original lens. Recently, there have been advances in IOL calculation methodologies that use intraoperative refraction devices, such as the Wavetec ORA and Orange systems, to provide better refractive outcomes. These devices can perform aphakic refractions, pseudophakic refractions, and assist with the alignment of toric IDLs and assist with Limbal Relaxing Incisions. Aphakic refractions do not have the benefit of any lens inside the eye, so ELP is still a variable that this data cannot account for. Pseudophakic refractions can be helpful, but it provides the information only after the IOL has been implanted. If the data shows a different lens would be more beneficial, it would require the physician to explants the lens and implant a different one. Explanting a lens takes time, effort and skill, and can cause damage to the cornea or other structures within the eye. Using a PPL-C 10 with a low power lens incorporated into its posterior surface, e.g., the posterior refractive surface 19, allows a physician to perform a pseudophakic refraction with this refractive surface, and still provides the physician the ability to implant a second lens, e.g., the IOL 28, within the PPL-C 10 that will make up the refractive difference as measured by the intraoperative refraction device, such as the Wavetec ORA.

Sixth, the PPL-C 10 may serve as a means for pharmaceutical delivery. Pharmaceuticals, drugs, medications, such as, for example, slow release medicine pellets, or other substances intended for introduction into the eye may be placed within PPL-C 10 outside of the visual axis 15 in a location that is not subject to sequestration by membrane formation. There is a tremendous amount of research and demand for a slow release implant that would essentially eliminate the need for post cataract surgery eye drops. The PPL-C 10 would be a suitable receptacle for such an implant as the periphery of the interior of the PPL-C provides a location outside of the visual axis 15, in constant contact with the aqueous humor, without risk of becoming encapsulated by scarring, and prevents the implant from damaging natural intraocular structures. Due to the prosthetic material of the PPL-C 10, there would be no risk of membrane formation or encapsulation. Dissolved or suspended pharmaceuticals would not affect the patient's vision and could be introduced directly into the PPL-C 10 during the implantation surgery. Larger pharmaceuticals, such as slow release medicine pellets, may be shaped to mechanically maintain their position with respect to the PPL-C 10. For example, a slow release medicine pellet may be constructed with a generally toroidal shape sized to fit within the PPL-C, while remaining in the peripheral space and not obstructing the visual axis 15.

Seventh, the PPL-C 10 provides physicians with the ability to perform a lens exchange in the future that will have much less risk of damage to the natural capsular bag 24 and zonular apparatus. As stated above, if a PPL-C 10 is placed in the natural capsular bag 24 and a YAG laser posterior capsulotomy has been performed, there is still an adequate barrier for the vitreous in place. In addition, the haptics 30 which hold the IOL 28 in place inside the PPL-C 10 are not prone to scar formation, thus making future lens removal much easier.

Figure 5:
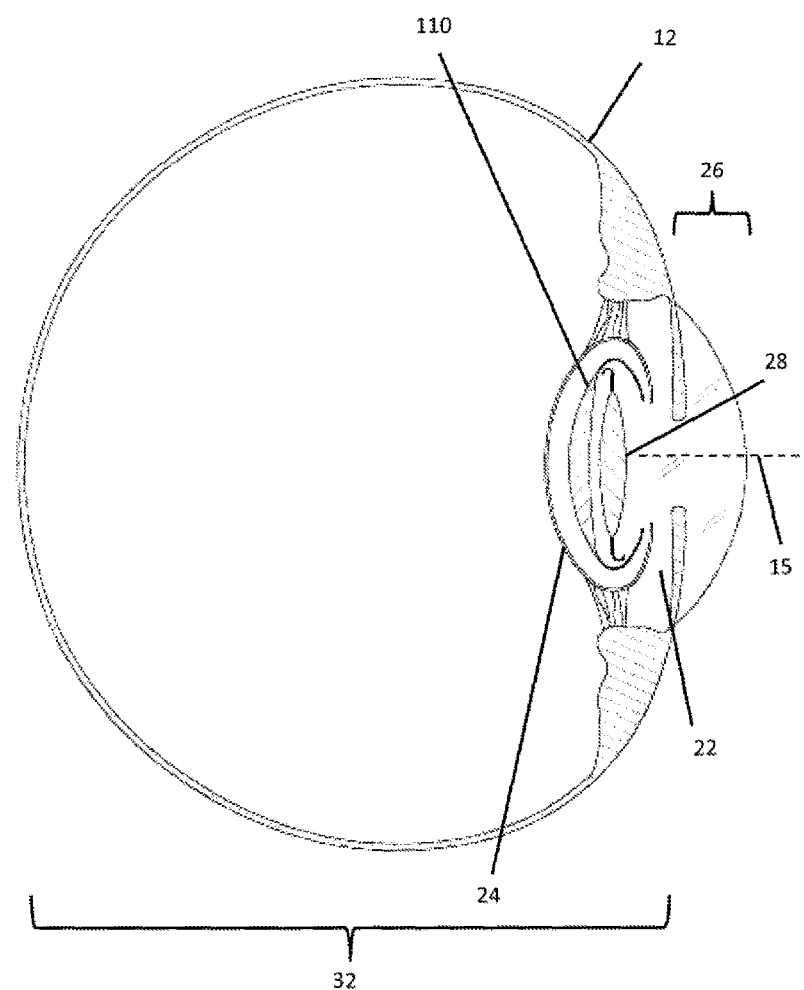
FIG. 5 depicts a cross-sectional side view of an eye including a second embodiment of a PPL-C containing an IOL.
Figure 6:
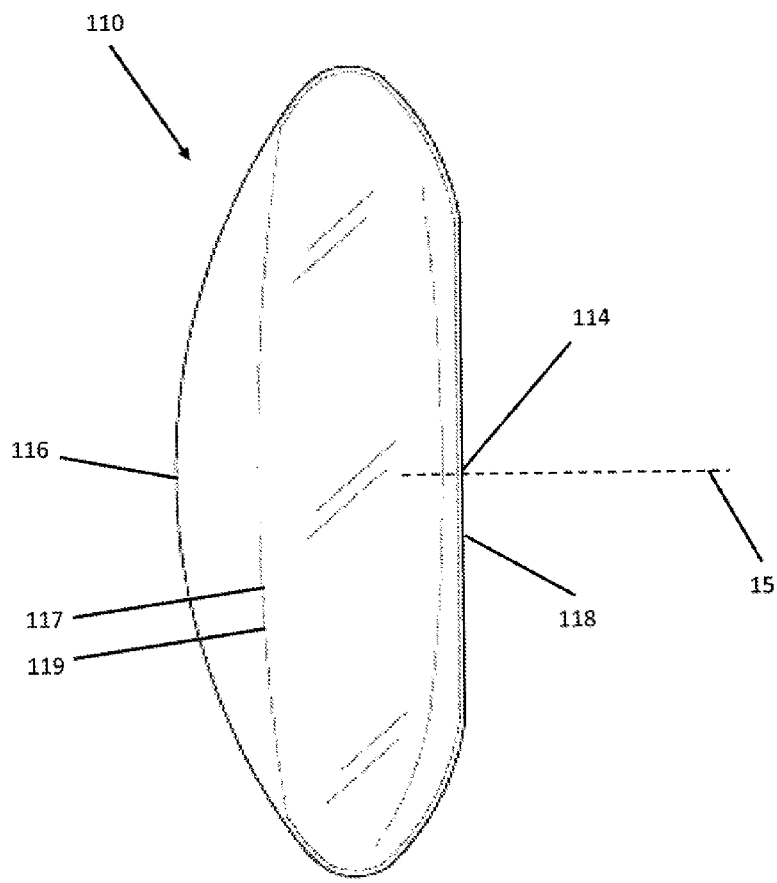
FIG. 6 depicts a side elevation view of the second embodiment of the PPL-C.
Figure 7:
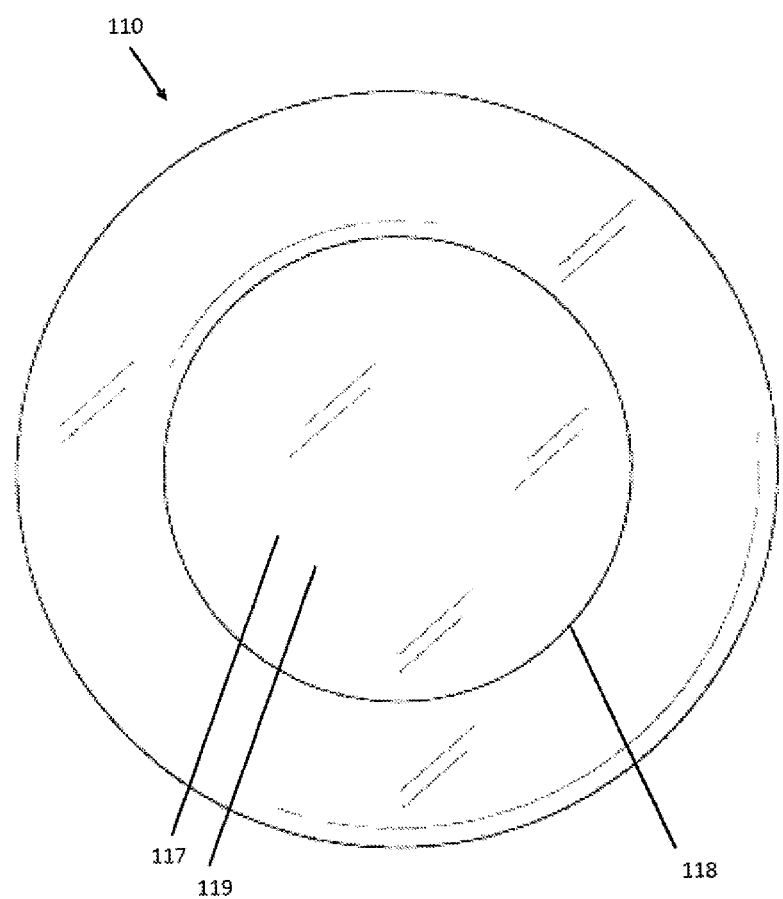
FIG. 7 depicts an anterior plan view of the second embodiment of the PPL-C.

FIGS. 5-7 depict a second embodiment of the present invention. In this embodiment, the PPL-C 110 is a substantially discoid shape of approximately 4.5 mm in thickness by 9 mm in diameter. The thickness of the PPL-C 110 is the distance between the anterior surface 114 and posterior surface 116 of the PPL-C 110 along the visual axis 15. The anterior surface 114 contains a circular opening 118 approximately 6 mm in diameter. At least a portion of the inner face 117 of the posterior surface 116 of the PPL-C 110 is made of a refractive surface, e.g. the posterior refractive surface 119. This second embodiment of differs from the first embodiment in that the PPL-C 110 lacks a flange and would therefore not be mechanically fixated or centered on the capsulorhexis. Rather, the volume of the PPL-C 110 relative to the opening of the capsulorhexis would keep the device in place much in the same way current single piece IDLs are folded and placed within the natural capsular bag.

This second embodiment PPL-C 110 sacrifices a measure of stability as compared to the first embodiment PPL-C 10. However, without a flange, this second embodiment is usable for non-femtosecond laser cataract removal, i.e. traditional manual phacoemulsification, and may be particularly useful for surgeons who lack access to a femtosecond laser.

In a third embodiment, the lenticular surface on the posterior aspect of the device would have a plano powered lens. Some extreme myopes would not benefit from a +1D refractive surface as they may be in need of a negative IOL power. For patients with these conditions, a PPL-C may be used with a plano or zero power posterior lenticular surface.

In a fourth embodiment, the PPL-C has a −1D posterior refractive lenticular surface as some extreme axial myopes (about 30 mm and beyond) may require this type of lens.

In a fifth embodiment, the posterior refractive surface 19 is a multifocal lenticular surface rather than a standard monofocal +1D surface, which would aid in presbyopia correction. This multifocal lenticular surface includes, but is not limited to, refractive, diffractive, and zonal multifocal refractive technology. Typically, a multifocal lens would be designed to provide multiple focal points that would range from plano, e.g., 0 diopters, to +3D at the spectacle plane.

In a sixth embodiment, the posterior refractive surface 19 includes a spherical and cylinderic (astigmatic) lenticular surface so as to aid in the correction of pre-existing and surgically induced corneal astigmatism. As most surgeons induce between −0.25 D and −0.50 D of astigmatism with their corneal incisions required for cataract surgery, it would be beneficial even for most patients with spherical corneas to have this neutralized. The diopteric power of the toric correction could increase up to 6 diopters for patients with even higher amounts of astigmatism.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. An ophthalmic surgical method for determining a desired intraocular lens for insertion into a prosthetic implant device implanted in a natural capsular bag of an eye after removal of a cataract, the ophthalmic surgical method comprising:

introducing the prosthetic implant device into the eye, wherein introducing the prosthetic implant device into the eye comprises allowing the prosthetic implant device to elastically resume a pre-folded shape, the prosthetic implant device comprising:
an anterior end;
a posterior end comprising a refractive surface having a refractive power;
sidewalls between the anterior end and the posterior end, the sidewalls at least partially defining a channel;
an anterior opening; and
an exterior contour;
using the exterior contour to stabilize and center at least a portion of the prosthetic implant device in a capsulorhexis;
using the prosthetic implant device to maintain a volume of the natural capsular bag;
performing a pseudophakic refraction to determine an effective lens position (ELP) of the refractive surface of the posterior end at least partially based on the refractive power of the refractive surface of the posterior end;
determining a refractive power of the desired intraocular lens for implantation into the prosthetic implant device, the determination at least partially based on the determined effective lens position (ELP) of the refractive surface of the posterior end of the prosthetic implant device;
selecting a first intraocular lens based on the determined refractive power of the desired intraocular lens; and
inserting the first intraocular lens into the channel through the anterior opening, the first intraocular lens comprising haptics engaging the sidewalls.

2. The ophthalmic surgical method of claim 1, further comprising:
removing the first intraocular lens from the prosthetic implant device through the anterior opening; and
exchanging the first intraocular lens with a second intraocular lens by implanting the second intraocular lens into the channel of the prosthetic implant device through the anterior opening.

3. The ophthalmic surgical method of claim 2, wherein the natural capsular bag is damaged.

4. The ophthalmic surgical method of claim 1, wherein the refractive power of the posterior refractive surface is between +30 diopters and −30 diopters.

5. An ophthalmic surgical method for determining a desired intraocular lens for insertion into a prosthetic device implanted in a natural capsular bag of an eye after removal of a cataract, the ophthalmic surgical method comprising:
introducing the prosthetic device into the eye, said prosthetic device comprising a posterior portion having a refractive surface having a refractive power, and the prosthetic device comprising a flange that extends therefrom, wherein introducing the prosthetic device into the eye comprises allowing the prosthetic device to elastically resume a pre-folded shape and to maintain a volume of the natural capsular bag;
inserting and fixating said flange into tissue of the eye;
performing a pseudophakic refraction to determine an effective lens position (ELP) of the refractive surface of the posterior portion at least partially based on the refractive power of the refractive surface of the posterior portion;
determining a refractive power of the desired intraocular lens for implantation into the prosthetic device, the determination at least partially based on the determined effective lens position (ELP) of the refractive surface of the posterior portion of the prosthetic device;

selecting a first intraocular lens based on the determined refractive power of the desired intraocular lens; and inserting the first intraocular lens into the prosthetic device, the intraocular lens comprising haptics engaging sidewalls of the first prosthetic device.

6. The ophthalmic surgical method of claim 5, wherein the prosthetic device comprises an anterior opening, and wherein inserting the first intraocular lens into the prosthetic device comprises inserting the first intraocular lens through the anterior opening.

7. The ophthalmic surgical method of claim 5, wherein the tissue of the eye comprises ciliary sulcus.

8. The ophthalmic surgical method of claim 5, wherein the natural capsular bag is damaged.

9. The ophthalmic surgical method of claim 5, further comprising:

removing the first intraocular lens from the prosthetic implant device; and exchanging the first intraocular lens with a second intraocular lens by implanting the second intraocular lens into the prosthetic implant device.

10. The ophthalmic surgical method of claim 5, wherein the refractive power of the posterior refractive surface is between +30 diopters and −30 diopters.

11. An ophthalmic surgical method for exchanging an intraocular lens from a prosthetic implant device in a natural capsular bag of an eye after removal of a cataract, the ophthalmic surgical method comprising:

introducing the prosthetic implant device into the eye, the prosthetic implant device comprising:

an anterior opening;

a posterior refractive surface; and sidewalls between the anterior opening and the posterior refractive surface, the sidewalls at least partially defining a channel, wherein introducing the prosthetic implant device into the eye comprises allowing the prosthetic implant device to elastically resume a pre-folded shape and to maintain a volume of the natural capsular bag;

selecting a first intraocular device based on a determined refractive power of a desired intraocular lens, the refractive power of the desired intraocular lens for implantation into the prosthetic implant device determined at least partially based on a determined effective lens position (ELP) of the posterior refractive surface of the prosthetic implant device, the effective lens position (ELP) of the posterior refractive surface determined at least partially based on a known refractive power of the posterior refractive surface;

inserting the first intraocular device into the channel of the prosthetic implant device through the anterior opening, the first intraocular device comprising haptics engaging the sidewalls of the prosthetic implant device;

removing the first intraocular device from the prosthetic implant device through the anterior opening; and exchanging the inserted first intraocular device with a second intraocular device by implanting the second intraocular device into the channel of the prosthetic implant device through the anterior opening.

12. The ophthalmic surgical method of claim 11, wherein the natural capsular bag is damaged.

13. The ophthalmic surgical method of claim 11, wherein the posterior refractive surface has an optical power between +30 diopters and −30 diopters.

14. The ophthalmic surgical method of claim 11, wherein introducing the prosthetic implant device into the eye comprises inserting the prosthetic implant device in a folded state through an incision.

15. The ophthalmic surgical method of claim 14, wherein the incision is between 1.5 mm and 3 mm.

16. The ophthalmic surgical method of claim 14, wherein inserting the prosthetic implant device in the folded state comprises using an injection system.

17. The ophthalmic surgical method of claim 16, wherein the injection system comprises a cylindrical cartridge and an advancement system.

18. The ophthalmic surgical method of claim 11, wherein selecting a first intraocular device comprises:

performing a pseudophakic refraction to determine the effective lens position (ELP) of the posterior refractive surface at least partially based on the known refractive power of the posterior refractive surface; and determining the refractive power of the desired intraocular lens for implantation into the prosthetic implant device, the determination at least partially based on the determined effective lens position (ELP) of the posterior refractive surface of the prosthetic implant device.

19. The ophthalmic surgical method of claim 18, further comprising confirming an effective lens position of the first intraocular device.

* * * * *

UNITED STATES PATENT AND TRADEMARK OFFICE
CERTIFICATE OF CORRECTION

| | | |
|---|---|---|
| PATENT NO. | : 9,439,754 B2 | |
| APPLICATION NO. | : 14/608654 | |
| DATED | : September 13, 2016 | |
| INVENTOR(S) | : Gary N. Wortz | |

It is certified that error appears in the above-identified patent and that said Letters Patent is hereby corrected as shown below:

On the Title Page

Page 1 (item (73), Assignee) at Line 1, Change "Opthalmics" to --Ophthalmics--.

In Column 2 (page 3, item (56)) at Line 11, Under U.S. Patent Documents, Change "Ophthalmologel," to --Ophthalmology,--.

In the Specification

In Column 2 at Line 51, Change "IOL." to --IOL;--.

In Column 4 at Line 28, Change "psuedophakic" to --pseudophakic--.

In Column 5 at Line 3, Change "psuedophakic" to --pseudophakic--.

In Column 6 at Line 24, Change "pupiloplasty," to --pupilloplasty,--.

In Column 8 at Line 19, Change "IDLs" to --IOLs--.

In Column 9 at Line 20, Change "IDLs" to --IOLs--.

In Column 9 at Line 47, Change "cylinderic" to --cylindrical--.

In Column 9 at Line 53, Change "diopteric" to --dioptric--.

In the Claims

In Column 12 at Line 45, In Claim 19, after "position" insert --(ELP)--.

Signed and Sealed this
Third Day of January, 2017

Michelle K. Lee
*Director of the United States Patent and Trademark Office*